United States Patent
Tiwari et al.

(10) Patent No.: US 10,531,950 B2
(45) Date of Patent: Jan. 14, 2020

(54) INTRAOCULAR LENS HAVING AN EXTENDED DEPTH OF FOCUS

(71) Applicant: Tatvum LLC, Irvine, CA (US)

(72) Inventors: Nivedan Tiwari, Irvine, CA (US); Krishnakumar Venkateswaran, Aliso Viejo, CA (US)

(73) Assignee: Tatvum LLC, Irvine, CA (US)

( * ) Notice: Subject to any disclaimer, the term of this patent is extended or adjusted under 35 U.S.C. 154(b) by 22 days.

(21) Appl. No.: 15/727,019

(22) Filed: Oct. 6, 2017

(65) Prior Publication Data

US 2018/0132996 A1    May 17, 2018

Related U.S. Application Data

(63) Continuation-in-part of application No. 15/353,381, filed on Nov. 16, 2016, now abandoned.

(51) Int. Cl.
*A61F 2/16*    (2006.01)

(52) U.S. Cl.
CPC .......... *A61F 2/1618* (2013.01); *A61F 2/164* (2015.04); *A61F 2/1616* (2013.01);
(Continued)

(58) Field of Classification Search
CPC .... A61F 2/1618; A61F 2/1654; A61F 2/1616; A61F 2/1627; A61F 2/164; A61F 2/1601;
(Continued)

(56) References Cited

U.S. PATENT DOCUMENTS

| 5,117,306 | A  | 5/1992 | Cohen  |
| 6,536,898 | B1 | 3/2003 | Cathey |

(Continued)

FOREIGN PATENT DOCUMENTS

| EP | 1424049 | 6/2004  |
| EP | 2113226 | 11/2009 |

(Continued)

OTHER PUBLICATIONS

D.P. Godwin, D.R. Selviah, C.D. Carey and J.E. Midwinter, The Self-Focusing Fresnel-Dammann Grating and the Fresnel Binary CGH for Compact 2-D Light Spot Array Generation, pp. 147-152, Department of Electronic and Electrical Engineering. University College London, UK.

(Continued)

*Primary Examiner* — David H Willse
*Assistant Examiner* — Tiffany P Shipmon
(74) *Attorney, Agent, or Firm* — Bond, Schoeneck & King, PLLC; Jeffrey Powers

(57) ABSTRACT

An intraocular lens, comprising an optic having an anterior surface and a posterior surface, providing a refractive base power, at least one of the anterior surface and the posterior surface having disposed thereon a profile comprising steps having heights determined by combining three constituent diffractive profiles. The diffractive profiles correspond to powers p1, p2 and p3, the powers being different than one another and each power being a positive power less than about 1D or about 1.25D. Each of the diffractive profiles having step heights causing a phase delay, relative to aqueous fluid, of 0.6 to 1.2 times $2\pi$ for 546 nm light. The combined profile defined by the function: z=max (diffractive profile (p1), diffractive profile (p2), diffractive profile (p3)), where p3>p2>p1.

25 Claims, 6 Drawing Sheets

(52) U.S. Cl.
CPC .......... *A61F 2/1627* (2013.01); *A61F 2/1654* (2013.01); *A61F 2/1601* (2015.04); *A61F 2002/1681* (2013.01); *G02C 2202/20* (2013.01)

(58) Field of Classification Search
CPC ........ A61F 2002/1681; G02B 27/0075; G02C 2202/20
See application file for complete search history.

(56) References Cited

U.S. PATENT DOCUMENTS

| | | | |
|---|---|---|---|
| 7,025,454 | B2 | 4/2006 | Cathey |
| 7,377,640 | B2 | 5/2008 | Piers |
| 7,377,641 | B2 | 5/2008 | Piers |
| 7,543,937 | B2 | 6/2009 | Piers |
| 7,670,371 | B2 | 3/2010 | Piers |
| 7,871,162 | B2 | 1/2011 | Weeber |
| 7,896,916 | B2 | 3/2011 | Piers |
| 8,157,374 | B2 | 4/2012 | Bandhauer |
| 8,231,219 | B2 | 7/2012 | Weeber |
| 8,292,953 | B2 | 10/2012 | Weeber et al. |
| 8,382,281 | B2 | 2/2013 | Weeber |
| 8,430,508 | B2 | 4/2013 | Weeber |
| 8,444,267 | B2 | 5/2013 | Weeber et al. |
| 8,480,228 | B2 | 7/2013 | Weeber |
| 8,500,805 | B2 | 8/2013 | Kobayashi et al. |
| 8,636,796 | B2 | 1/2014 | Houbrechts et al. |
| 8,678,583 | B2 | 3/2014 | Cohen |
| 8,740,978 | B2 | 6/2014 | Weeber et al. |
| 8,747,466 | B2 | 6/2014 | Weeber et al. |
| 8,862,447 | B2 | 10/2014 | Weeber |
| 8,894,204 | B2 | 11/2014 | Weeber et al. |
| 9,069,185 | B2 | 6/2015 | Zhao |
| 9,134,543 | B2 | 9/2015 | Zalevsky et al. |
| 9,216,080 | B2 | 12/2015 | Bogaert et al. |
| 9,223,148 | B2 | 12/2015 | Fiala et al. |
| 9,304,329 | B2 | 4/2016 | Zhao |
| 9,335,563 | B2 | 5/2016 | Weeber |
| 9,454,018 | B2 | 9/2016 | Weeber et al. |
| 9,557,580 | B2 | 1/2017 | Weeber |
| 9,636,214 | B2 | 5/2017 | Piers |
| 2008/0300679 | A1 | 12/2008 | Altmann |
| 2009/0187242 | A1* | 7/2009 | Weeber .................. A61F 2/1654 623/6.24 |
| 2009/0210054 | A1 | 8/2009 | Weeber |
| 2011/0149236 | A1 | 6/2011 | Weeber |
| 2011/0267693 | A1 | 11/2011 | Kobayashi et al. |
| 2011/0292335 | A1 | 12/2011 | Schwiegerling |
| 2012/0140166 | A1 | 6/2012 | Zhao |
| 2012/0165932 | A1 | 6/2012 | Argal et al. |
| 2013/0226294 | A1 | 8/2013 | Van Der Mooren |
| 2014/0168602 | A1 | 6/2014 | Weeber |
| 2014/0172088 | A1 | 6/2014 | Carson et al. |
| 2014/0257480 | A1 | 9/2014 | Van Der Mooren |
| 2016/0100938 | A1 | 4/2016 | Bogaert et al. |
| 2016/0216535 | A1 | 7/2016 | Zhao |
| 2016/0320633 | A1 | 11/2016 | Weeber |
| 2017/0227789 | A1 | 8/2017 | Ando et al. |

FOREIGN PATENT DOCUMENTS

| | | |
|---|---|---|
| EP | 2180849 | 5/2010 |
| EP | 2283392 | 2/2011 |
| EP | 2334260 | 6/2011 |
| EP | 2363097 | 9/2011 |
| EP | 2365379 | 9/2011 |
| EP | 2512371 | 10/2012 |
| EP | 2512372 | 10/2012 |
| EP | 2564263 | 3/2013 |
| EP | 2564264 | 3/2013 |
| EP | 2649487 | 10/2013 |
| EP | 2651334 | 10/2013 |
| EP | 2747706 | 7/2014 |
| EP | 2890287 | 7/2015 |
| WO | WO2011024125 A1 | 3/2011 |
| WO | 206021075 | 2/2016 |

OTHER PUBLICATIONS

International Search Report and Written Opinion, International Application No. PCT/US2017/061765, pp. 1-12, International Filing Date Nov. 15, 2017, Search Report dated Feb. 13, 2018.

* cited by examiner

# INTRAOCULAR LENS HAVING AN EXTENDED DEPTH OF FOCUS

RELATED APPLICATIONS

This application is a continuation-in-part of U.S. application Ser. No. 15/353,381 filed Nov. 16, 2016, titled INTRAOCULAR LENS HAVING AN EXTENDED DEPTH OF FOCUS, the substance of which is hereby incorporated by reference in its entirety.

FIELD

Intraocular lenses, and in particular intraocular lenses providing an extended depth of focus.

BACKGROUND

Intraocular lenses (IOLs) comprising an optic and, perhaps, one or more haptics for positioning the optic within an eye are known. One type of IOL providing a range of vision including distance vision, intermediate vision and/or near vision is multifocal lenses. Conventional multifocal lenses typically fit into one of two classes.

The first class of multifocal lenses is referred to as refractive multifocal, in which an optic is divided into multiple refractive zones and light from a particular zone is directed to only one of the foci using only refractive power. The zones can be concentric about the optical center or non-axis-symmetric. Refractive multifocal lenses form two or more foci to provide far, intermediate and/or near vision.

The second class of multifocal lenses is referred to as diffractive multifocal. Such lenses include a diffractive element comprising radial zones that transmit light that is out of phase with light transmitted through adjacent zones (i.e., there is a phase delay between adjacent zones). Like refractive multifocal lenses, diffractive multifocal lenses form two or more foci to provide far, intermediate and/or near vision. In diffractive multifocal lenses, the radial boundaries that separate the zones are chosen to achieve particular optical powers.

Both diffractive multifocal and refractive multifocal lens techniques for extending range of vision have resulted in IOLs having distinct foci where vision is sharp, and regions of poorer focus between the foci. A well-known example of a figure of merit for measuring the performance of visual systems is known as a Modulation Transfer Function (commonly referred to as an "MTF"). An MTF of an optical system is a measure of the proportion of contrast of an input object that the optical system is able to maintain when an image of the object is produced. An MTF can be measured as a function of spatial frequency (e.g., line pairs per mm at the retina). Generally, the MTF values for a given optical system decrease with an increase in the spatial frequency.

For a given spatial frequency, each foci of a IOL (i.e., near, intermediate or far focus) manifests itself in a through-focus MTF plot as a peak in MTF values, with regions of lower MTF values between the peaks. For an individual wearer of an IOL, a region of lower MTF values may be large enough to permit vision depending on the broadening and flattening of MTF peaks that occurs for the individual due the ocular aberrations of the individual's eye and his/her pupillary response.

While multifocal lenses are known to provide a beneficial increase in the range of vision of a wearer, a significant proportion of wearers of IOLs employing these multifocal techniques have been known to suffer visual confusion and photic phenomena (i.e., unwanted artifacts in an image formed by pseudophakic eyes) due to the presence of multiple sharply-focused images simultaneously formed on their retinas.

As an alternative to multifocal lenses, techniques for extending the depths of focus of monofocal IOLs (i.e., without multiple peaks in the MTF curve) to obtain distance vision as well as nearer vision have been proposed. IOL techniques to provide an extended depth of focus (EDOF) include: a) providing an IOL with a central refractive add zone; b) providing an IOL with high magnitude positive or negative spherical aberration; and c) providing an underlying refractive IOL with a relatively low-power add diffractive profile (i.e., a diffractive add of 1.5 Diopter or less). Each such extended depth of focus technique has provided limited improvement to wearers' visual quality.

Conventionally, low-power, diffractive add profiles have been selected such that the phase delay between adjacent zones is 0.5 wavelengths of a design wavelength (e.g., approximately 550 nm for visible light). One example of such a lens is described in U.S. Pat. No. 8,747,466. Such lenses tend to provide a high degree of multifocality, such that light is evenly divided between a central focus corresponding to a zeroth order of the diffractive profile, and a near and a far focus corresponding to a +1 order and a -1 order of the diffractive profile, respectively. Such lens configurations tend to cause multiple peaks in the MTF. However, even when the IOL is designed such that the MTF is flattened to eliminate peaks, such designs tend to direct light symmetrically about a central focus to each of the near and far foci, resulting in inefficient use of light energy, without a peak at far vision, and lens performance may be compromised.

According to other diffractive design techniques, the phase delay between adjacent zones has been decreased to a value between 0.4 and 0.5 of a wavelength. Such designs tend to reduce the bifocality of the lens by decreasing the percentage of light sent to the near focus in favor light sent to the far focus since wearers of multifocal lenses tend to prefer peak vision performance for distance vision. Such lenses suffer from similar drawbacks as the more bifocal lenses with regard to presence of multiple peaks in MTF.

Accordingly there remains a need for alternative techniques for extending the depth of focus of ophthalmic lenses without multiple peaks in the MTF curves of resultant lenses and more efficient use of light energy.

BRIEF SUMMARY

According to aspects of the present invention, in order to prevent or reduce the likelihood of photic phenomena in an EDOF lens, it has been determined that it is preferable to use a monofocal IOL having a best focus for far vision and a depth of focus extending toward an intermediate range. The through-focus MTF curve of such a "monofocal IOL with extended depth of focus" is designed such that there is a single peak (i.e., a single local maximum) corresponding to far vision (also corresponding to the absolute maximum) and, for positive add powers from the maximum single peak (i.e., the myopic side of best focus), no additional peaks between the single peak and the first zero (defined below) in the MTF. There is a decreasing yet visually-useful level of MTF extending in the myopic direction from the peak. In such embodiments, the MTF is non-increasing until the first zero in MTF is reached. In some embodiments, it is beneficial to the goal of reducing photic phenomenon that the MTF is monotonically decreasing until a first zero in the MTF is reached.

To achieve such performance, embodiments of the present invention comprise a refractive lens having a diffractive profile disposed thereon. The diffractive profile is comprised of a combination of at least three (i.e., three or more) diffractive profiles, each having a power of less than 1 D. The diffractive profiles have different optical powers. The three profiles are combined by taking the maximum of the three profiles at each radial position on the lens. To facilitate the spreading of the energy along the depth of focus, the step heights of the diffractive profiles may be selected to have a phase delay, relative to aqueous fluid (of a same depth as a given step height), of 0.6 to 1.2 times $2\pi$ for 546 nm light, which in conjunction with the "max" technique of combining the profiles tends to spread the light along the depth of focus.

An aspect of the invention is directed to an intraocular lens comprising an optic having an anterior surface and a posterior surface that provide a refractive base power. At least one of the anterior surface and the posterior surface has disposed thereon a combined profile comprising steps having heights determined by combining three constituent diffractive profiles. The constituent diffractive profiles corresponding to powers p1, p2 and p3, the powers being different than one another and each power being a positive power less than about 1D. Each of the constituent diffractive profiles has step heights causing a phase delay relative to aqueous fluid of 0.6 to 1.2 times $2\pi$ for 546 nm light. The combined profile defined by the function z=max (diffractive profile (p1), diffractive profile (p2), diffractive profile (p3)), where p3>p2>p1.

In some embodiments, the combined profile is disposed completely on the anterior surface of the lens. The combined profile may be disposed piecewise on both the anterior surface and posterior surface of the lens. The combined profile may be rotationally symmetric.

In some embodiments, the zones of the lens formed by the three constituent profiles are kinoform in shape.

In some embodiments, each of the constituent diffractive profiles has step heights causing a phase delay, relative to aqueous fluid, of 0.8 to 1.0 times $2\pi$ for 546 nm light.

The central zone may have a refractive surface having a shape independent of the constituent diffractive profiles. In some embodiments, the ratio of $p_1$ to $p_2$ is about 0.6, and the ratio $p_1$ to $p_3$ is about 0.4. In some embodiments, the ratio of $p_1$ to $p_2$ is about 0.67, and the ratio $p_1$ to $p_3$ is about 0.31. In some embodiments, the depth of focus is greater than 0.85 diopters.

Another aspect of the invention is directed to an intraocular lens comprising an optic having an anterior surface and a posterior surface that provide a refractive base power. At least one of the anterior surface and the posterior surface has disposed thereon a combined profile comprising steps having heights determined by combining three constituent diffractive profiles. The constituent diffractive profiles corresponding to powers p1, p2 and p3, the powers being different than one another and each power being a positive power less than about 1D. Each of the constituent diffractive profiles has step heights causing a phase delay relative to aqueous fluid of 0.6 to 1.2 times $2\pi$ for 546 nm light. The combined profile defined by the function z=max (diffractive profile (p1), diffractive profile (p2), diffractive profile (p3)), where p3>p2>p1. Embodiments, according to this aspect may have embodiments, as set forth above.

Another aspect of the invention is directed to a set of intraocular lenses, comprising at least three lens, each lens is configured according to an aspects or embodiment set forth above. Each of the lenses of the set has a different refractive, base dioptric power than one another. The range of the refractive base powers is at least 10 diopters across the set of lenses, and the combined profile of each of the at least three lenses is the same as each of the other lenses of the set.

The term "depth of focus" is defined herein to be the focal range of an IOL, measured from its through focus MTF absolute maximum peak toward the myopic direction, over a range for which the MTF at 50 lines pairs per mm through a 3 mm aperture in Model Eye 1 of ISO 11979-2 2014 is greater than 0.2 MTF units. Clinical studies using multifocal IOLs, that have slightly less than 0.2 MTF units measured at 50 lp/mm at one of their foci have shown that 50% of the patients had visual acuity between 20/28 and 20/20 and 40% of patients had 20/20 or better and a combined 90% better than 20/28. This finding leads to the conclusion that a majority of the patients will have 20/28 vision or better with an 0.2 MTF units at 50 lp/mm. Based on this clinical data, a criterion for depth of focus of an IOL can be defined as the range around the IOL focus where the 50 lp/mm MTF value is greater than 0.2 MTF units. A 3 millimeter pupil diameter is assumed for the above calculations and other calculations herein.

It is to be appreciated that, in some instances, to fully characterize an optical system (e.g., an ocular system) MTF may need to be measured along two orthogonal axes. In examples described herein, rotational symmetry is assumed. However, it is to be appreciated that asymmetric lenses may incorporate design principles according aspects of the present invention and is within the scope of aspects of the present inventions.

The term "anterior", when used herein with reference to an intraocular lens, refers to a feature on the lens tending toward the direction of the cornea of an eye in which the lens to be implanted, and term "posterior" refers to a feature on the lens tending toward on the retina of the eye.

A wavelength of light specified in nanometers (nm) herein refers to the wavelength when said light is propagated in vacuum. For example, 546 nm light refers to light having a wavelength of 546 nm when propagating in a vacuum although the wavelength of said light would deviate from 546 nm when propagated in a lens or a fluid of the eye due to the index of refraction of the lens and fluid.

The term "monofocal" as used herein refers to a lens having a single peak (i.e., a single local maximum; and the single peak also being the absolute maximum) in the MTF before a first zero in the MTF is reached for positive add powers.

The term "first zero" is defined herein to mean a first local minimum after the absolute maximum (i.e., best focus) in a through-focus MTF plot, on the myopic side, the local minimum having a value of less than 0.1 MTF units.

Performance measurements (e.g., through-focus MTF shape, including depth of focus) of a lens as described herein, as well as for determining the performance of other lenses and the scope of the claims, are/is to be performed by locating the lens in ISO 11979-2 2014 Model Eye 1.

BRIEF DESCRIPTION OF THE DRAWINGS

The nature and mode of operation of the present invention will now be more fully described in the following detailed description of the invention taken with the accompanying drawing figures, in which.

DETAILED DESCRIPTION

The inventor has discovered an unexpected result of combining multiple low-power diffractive profiles corresponding to different add powers using a "max function", to form a diffractive profile for use with an intraocular lens. Embodiments of such lenses provide the lens with a depth of focus having a single peak and significant spreading of optical energy along the optical axis of the lens to provide a visually-useful, extended depth of focus with no or a reduced likelihood of photic phenomenon.

Figure 1:
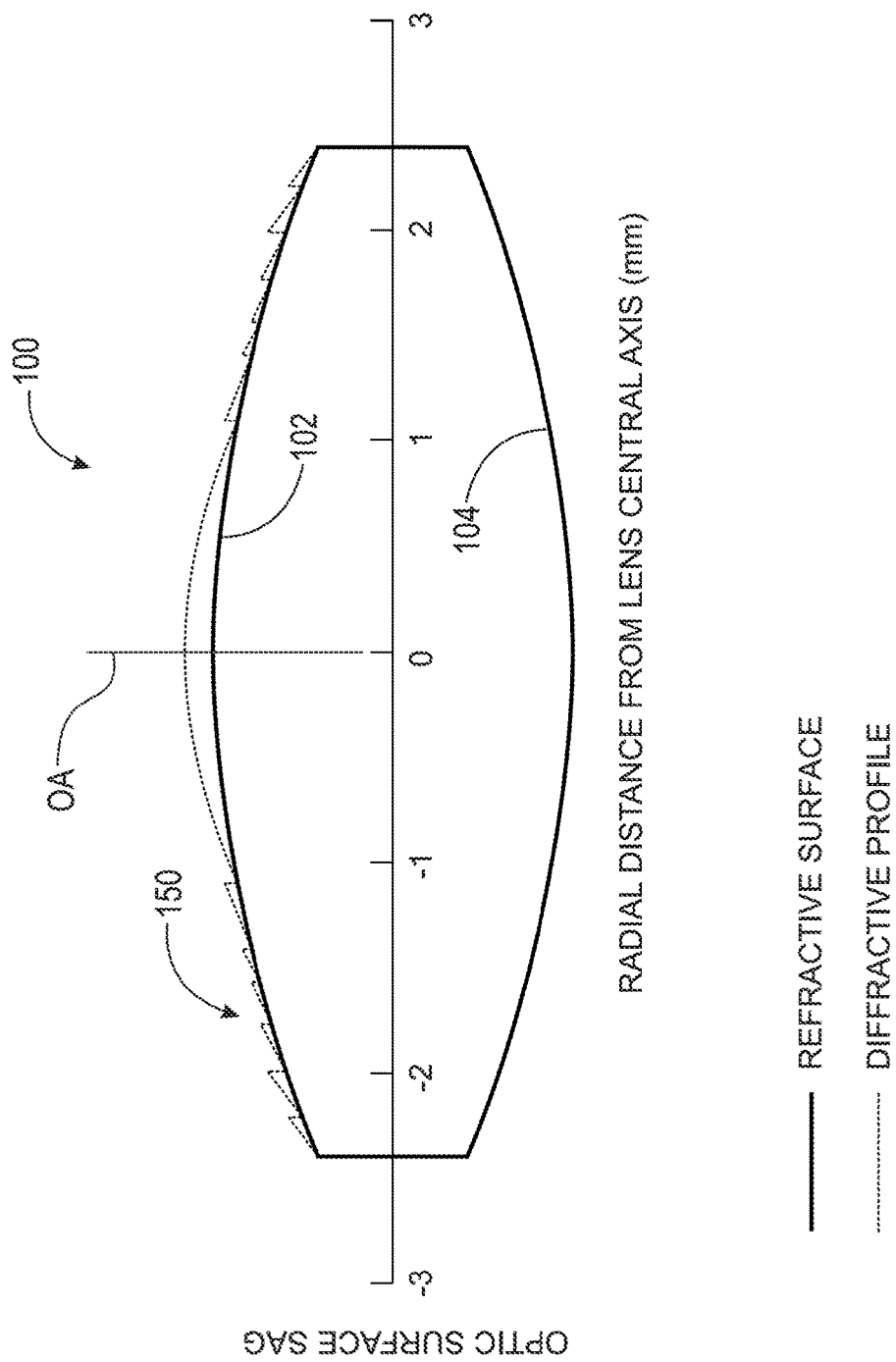
FIG. 1 is a schematic cross-sectional view of an example of an optical element of an intraocular lens including a combined diffractive profile according to aspects of the present invention, where the diffractive profile is magnified to facilitate discussion.

FIG. 1 is a schematic cross-sectional view of an example of an optical element 100 of intraocular lens (shown in FIG. 6) including a combined diffractive profile 150 according to aspects of the present invention. Optical element 100 has an anterior surface 102 and a posterior surface 104, providing a refractive power (commonly referred to as a "base power" of the lens). The refractive surfaces 102, 104 of the intraocular lens can be either spherical or aspheric, and may be bi-convex, as shown in FIG. 1, or may be plano-convex, meniscus or any other suitable shape. The value zero along the horizontal axis corresponds to the optical axis OA of the lens. Combined diffractive profile 150 may be applied to a base refractive lens having any suitable positive or negative dioptric value or a dioptric value of zero.

In the illustrated embodiment, anterior surface 102 has a profile comprising steps having heights $h_1, h_2 \ldots h_n$ resulting from combining three diffractive profiles superimposed thereon. Further details of forming a combined diffractive profile are given below.

Each of the three diffractive profiles corresponds to a respective power p1, p2 and p3. The powers have different magnitudes than one another. In some embodiments, each power has a positive power that is less than about 1D. In some of the embodiments, each power has a positive power that is less than about 1.25D. Each of the diffractive profiles has step heights causing a phase delay, relative to aqueous fluid, of 0.6 to 1.2 times 2π for 546 nm light. The combined profile is defined by the function:

$$z = \max(\text{diffractive profile}(p1), \text{diffractive profile}(p2), \text{diffractive profile}(p3))$$

where p3>p2>p1.

Although in the illustrated embodiment the combined diffractive profile is disposed on the anterior surface of the lens, the combined diffractive profile can be positioned completely on either the posterior surface or the anterior surface (as shown in FIG. 1). Alternatively, the combined profile can be positioned piece-wise on both refractive sides of the optical element. For example, a combined profile can be divided into multiple segments using lines that are parallel to the optical axis. Each segment of the profile can be located on the anterior surface of the lens or the posterior surface, while maintaining its corresponding radial location between given parallel lines.

It will be appreciated that the diffractive step heights in FIG. 1 are greatly magnified relative to the remainder of optical element 100 for ease of viewing. Additionally, the sharpness of the steps is exaggerated for the purpose of illustration. It will be appreciated that some rounding of the corners of the steps may occur due to manufacturing process. This smoothening could be due to, for example, lens or lens-mold machining or subsequent lens polishing processes. Such smoothening is not expected to degrade lens performance unless excessive so as to unacceptably diminish the lenses depth of focus or monofocality.

Further details of an IOL including an optical element as described herein and positioning of such an IOL in an eye are given with reference to FIG. 6 below.

Figure 2:
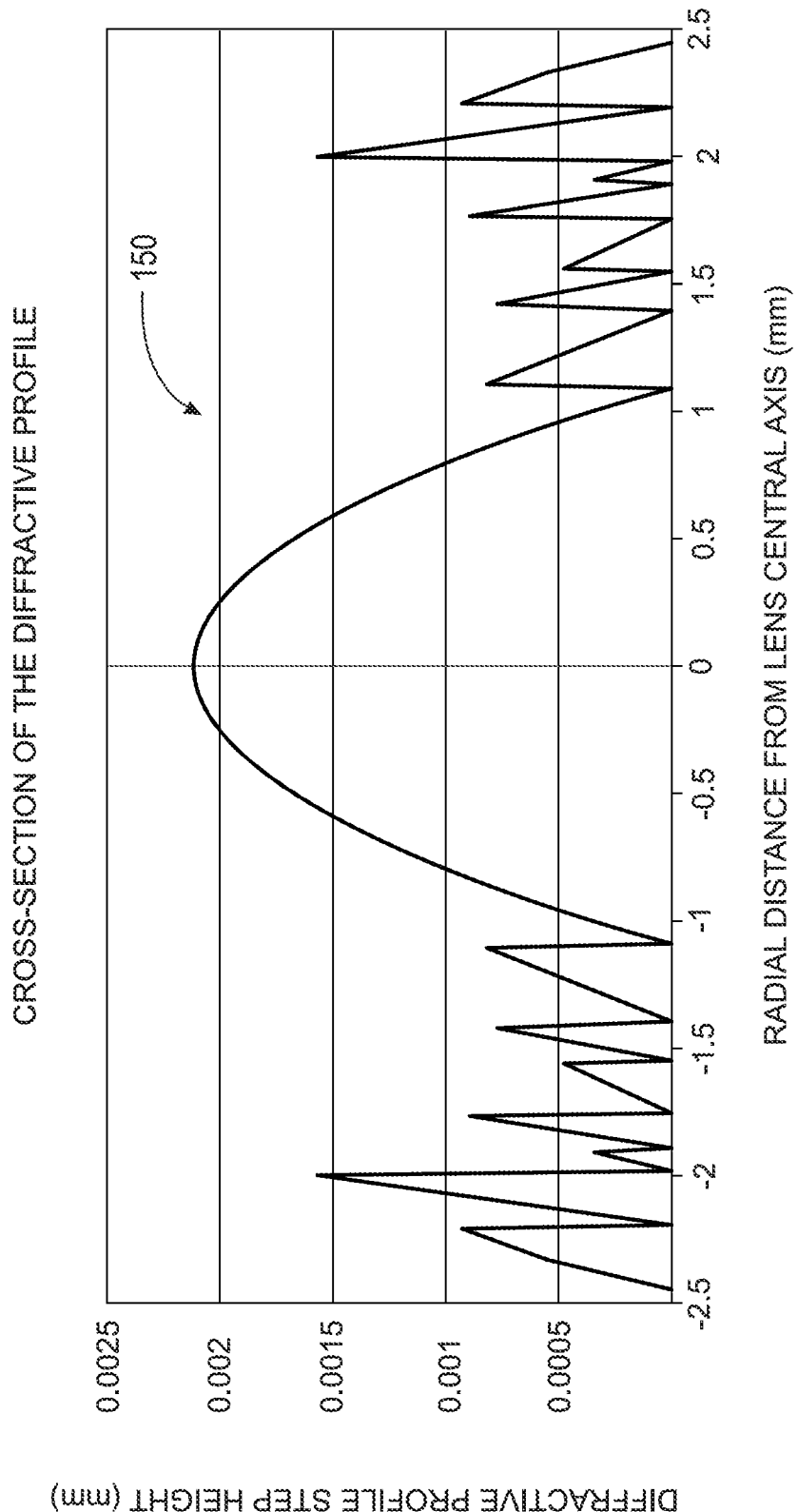
FIG. 2 is a cross-sectional view of the axially-symmetric, diffractive profile of the optical element of FIG. 1 as a function of radial distance, the diffractive profile being separated from the refractive surface.

FIG. 2 illustrates the combined, diffractive profile 150 of the optical element of FIG. 1 in greater detail. The profile is illustrated as a profile height as a function of radial location, the diffractive profile being separated from the refractive surface 102 (i.e., zero on the vertical axis corresponds to the anterior surface of the base refractive lens). It will be appreciated that the diffractive profile of FIG. 2 is rotationally symmetric about the optical axis OA. Although the profile has eight zones, any suitable number of zones may be used.

Figure 3:
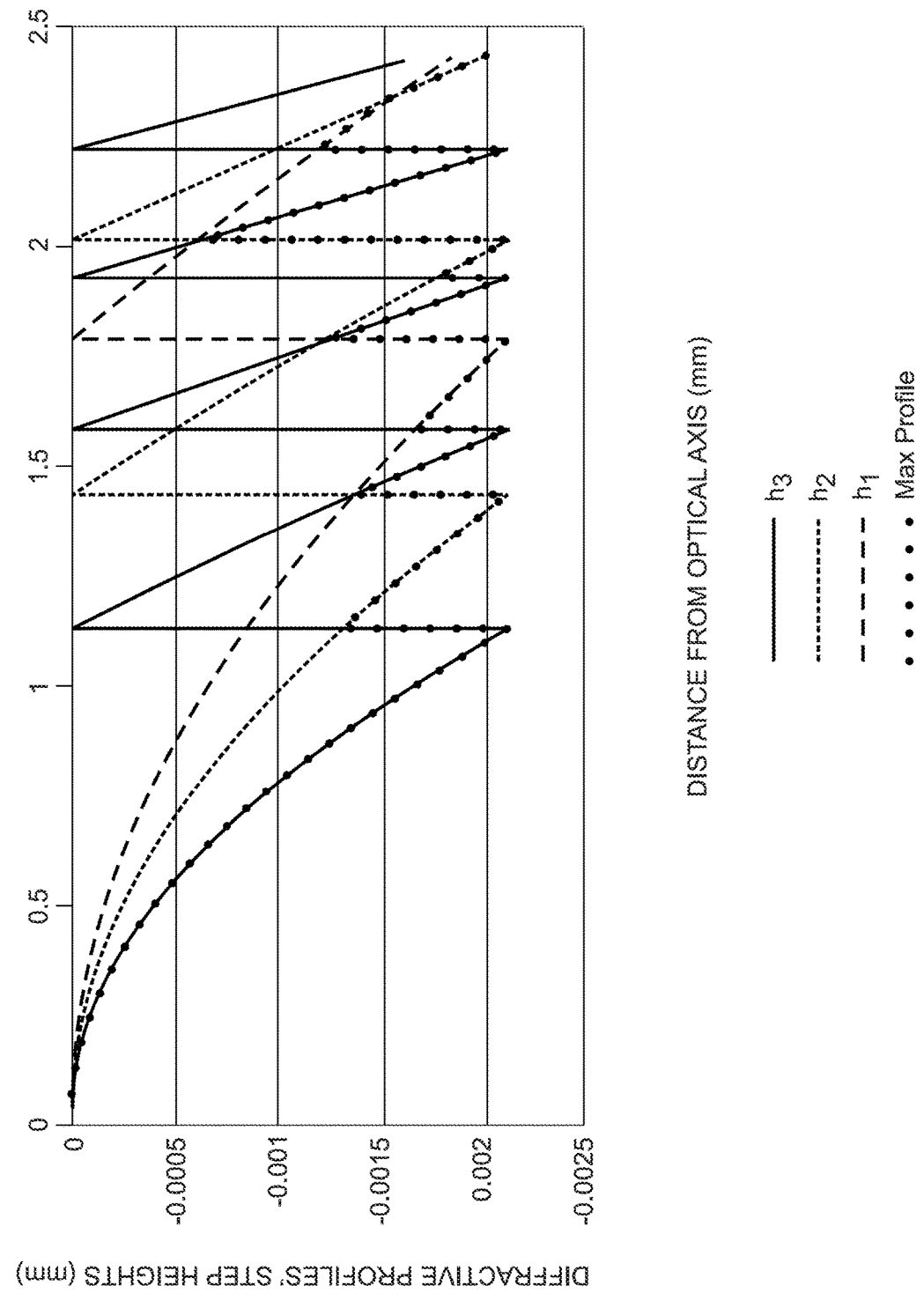
FIG. 3 is a cross-section illustration of the constituent diffractive profiles that are to be combined to produce the combined diffractive profile of FIG. 2.

FIG. 3 illustrates the individual, constituent diffractive profiles corresponding to powers $p_1$, $p_2$ and $p_3$, respectively that are combined to produce the combined diffractive profile of FIG. 2. The combined diffractive profile of FIG. 2 is produced by combining three, individual kinoform-type profiles. The three individual diffractive profiles corresponding to $p_1$, $p_2$, $p_3$ are defined in equations 1(a), 1(b) and 1(c), respectively.

$$h_1(r) = \frac{\lambda \eta}{(n_l - n_m)} \left\{ \left( \frac{r^2}{2F_1 \lambda} \right) - m_1 \right\} \quad \text{Equation 1(a)}$$

$$h_2(r) = \frac{\lambda \eta}{(n_l - n_m)} \left\{ \left( \frac{r^2}{2F_2 \lambda} \right) - m_2 \right\} \quad \text{Equation 1(b)}$$

$$h_3(r) = \frac{\lambda \eta}{(n_l - n_m)} \left\{ \left( \frac{r^2}{2F_3 \lambda} \right) - m_3 \right\} \quad \text{Equation 1(c)}$$

where:

r is the distance from the optical axis,

λ is the design wavelength of light in vacuum. In the examples provided herein, the wavelength is chosen to be 546 nm where the photoreceptors in the human eye are most sensitive, $n_1$ and $n_m$ are refractive indices of the lens material and the surrounding medium, respectively, at the design wavelength of 546 nm. In the examples provided herein, the lens refractive index value and the aqueous humor refractive index value are 1.5404 for $n_1$ and 1.336 for $n_m$, respectively. In the example of FIG. 3, the lens material is a hydrophobic acrylic. Other materials may be used to achieve designs according to aspects of the present invention, such as hydrophilic acrylic, polymethyl-methacrylate (PMMA) or silicone where the zone heights are chosen to achieve suitable phase delays.

η is a constant signifying the fraction of a 2π phase delay to be caused by light passing through the lens material relative to the same light traveling through the same thickness in the surrounding medium (e.g., aqueous fluid). A value of 0.8 for η has been used to derive the diffractive profiles in FIG. 3. While in some embodiments (such as those in the example of FIG. 3) η is the same for all profiles constituting the combined profile, the value of η for a constituent profile of a combined profile may be different than one or all of the other constituent profiles of the combined profile.

$F_1$, $F_2$ and $F_3$ are the focal lengths corresponding to the powers $p_1$, $p_2$, and $p_3$ chosen for creating profiles $h_1(r)$; $h_2(r)$, and $h_3(r)$ respectively. $F_1$, $F_2$ and $F_3$ are given by the reciprocals of powers $p_1$, $p_2$ and $p_3$ respectively. For the profiles in FIG. 3, the values of $p_1$, $p_2$ and $p_3$ are 0.35D, 0.55D and 0.9D.

$m_1$, $m_2$ and $m_3$ each take integer values 0, 1, 2 . . . signify the diffractive zone number. 0 indicates the central zone.

Although the embodiments described herein use kinoform profiles, it will be appreciated that other profiles may be used. For example, a linear profile such as a linear approximation to the kinoform shape, or other suitable approximations or shapes may be used. Also, although the example includes three constituent profiles in the combined profile, three or more constituent profiles may be used to form the combined profile. In embodiments having four or more constituent profiles, the fourth and any additional constituent profiles would have different powers than all other profiles, would have a power less than about 1 diopter (or less than about 1.25 diopters), and would be combined with the other profiles using the max function as described above.

Zone boundaries of the zones of the profile shown in FIG. 3 are given by equation 2:

$$r_m^2 + F^2 = \{(m+1)\lambda + F\}^2 \qquad \text{Equation 2}$$

where:

m indicates the zone number,

F is the focal length (as indicated above), $r_m$ is the radial zone boundary for the zone number m, and λ is the wavelength of light in a vacuum.

The constituent diffractive profiles are combined using a maximum function as shown in equation 3 to form the combined diffractive profile shown in FIG. 2.

$$z(r) = \text{Max}\{h_1(r), h_2(r), h_3(r)\} \qquad \text{Equation 3}$$

The values of z(r) that constitute a combined profile are taken as the maximum value (i.e., maximum thickness) of $h_1(r)$; $h_2(r)$, and $h_3(r)$, at each radial position r. As illustrated in FIG. 3, the thicknesses are measured as a deviation from zero in the negative direction. However, any convenient representation of thickness may be used.

The depth of the constituent profiles in FIG. 3 is 2.136 microns, which converts to a phase imparted upon transmission of about 0.8 wavelengths, or about 288 degrees of phase. A parabolic profile associated with the kinoform shape extends across all zones, with a step discontinuity at the edge of each zone.

The resulting combined profile in FIG. 2 is superimposed on a base refractive surface to form the optical element shown in FIG. 1. The superimposed shape is formed by adding the sagittal height of the refractive lens with the height of the combined diffractive profile at each radial position. In the example embodiment, the base refractive lens is a 20 diopter, biconvex lens having asphericity to substantially eliminate spherical aberration. The lens specification is as follows—1) an anterior surface radius of 20.0 mm with an aspheric $4^{th}$ order coefficient of $-1.58 \times 10^{-4}$, 2) a posterior IOL surface radius of 20.807 mm, and 3) an optic center thickness of 0.553 mm.

The inventor has noted that ratios of $p_1$ to $p_2$ and $p_1$ to $p_3$ of about 0.6 and 0.4 respectively, yield a depth of focus where the MTF smoothly rolls off from a maximum with no additional local maximum between the peak and the first zero in the MTF curve. While in the illustrated embodiments the powers are 0.35D, 0.55D and 0.9D, other powers where $p_1$ to $p_2$ is about 0.6, and the ratio $p_1$ to $p_3$ is about 0.4, and the powers are less than 1 diopter may be chosen. Other ratios of $p_1$ to $p_2$ and $p_1$ to $p_3$ of about 0.67 and 0.31 respectively, have also been found to yield a depth of focus where the MTF smoothly rolls off from a maximum with no additional local maximum between the peak and the first zero in the MTF curve. For example, $p_1$=0.39D, p2=0.58D and $p_3$=1.25D may be used.

It is to be appreciated that, in the illustrated embodiments, the zones are blazed which yields an asymmetric MTF curve, having a greater amount of energy being delivered the corneal/anterior side of the lens. While blazing may be advantageous in some embodiments, it is not necessary.

While embodiments with profiles having step heights causing a phase delay (relative to aqueous fluid) of 0.6 to 1.2 times 2π for 546 nm light generate solutions with a single maximum and no additional local maximum before the first zero in the MTF, for some combinations of profiles calculated or experimental testing of the resulting lens may be desirable to confirm that a monofocal lens with a substantial depth of focus is generated. Lens embodiments with profiles having step heights causing a phase delay, relative to aqueous fluid, of 0.8 to 1.0 times 2π for 546 nm light provide monofocal lenses with an extended depth of focus more consistently. It is to be appreciated that lenses according to aspects of the present invention have a phase delay between adjacent values of greater than the 0.6 of a wavelength as compared to conventional lenses which have a phase delay of 0.5 or less as described above. While phase delays of greater than 0.6 are generally thought to provide greater light to a near focus, which has been avoided in conventional designs, the inventor has found that such designs enhance depth of focus, particularly when used in combination with a diffraction profile resulting from multiple diffraction profiles combined using a max function as described herein.

Furthermore, it is to be appreciated that the above range of phase delays between adjacent zones includes phase delay of 1.0 which is conventionally associated with a high degree of monofocality. Again, the inventor has found that, due to the use of the max function, the three profiles combined using the max function permits distribution of light in a manner that enhances depth of focus.

Figure 4:
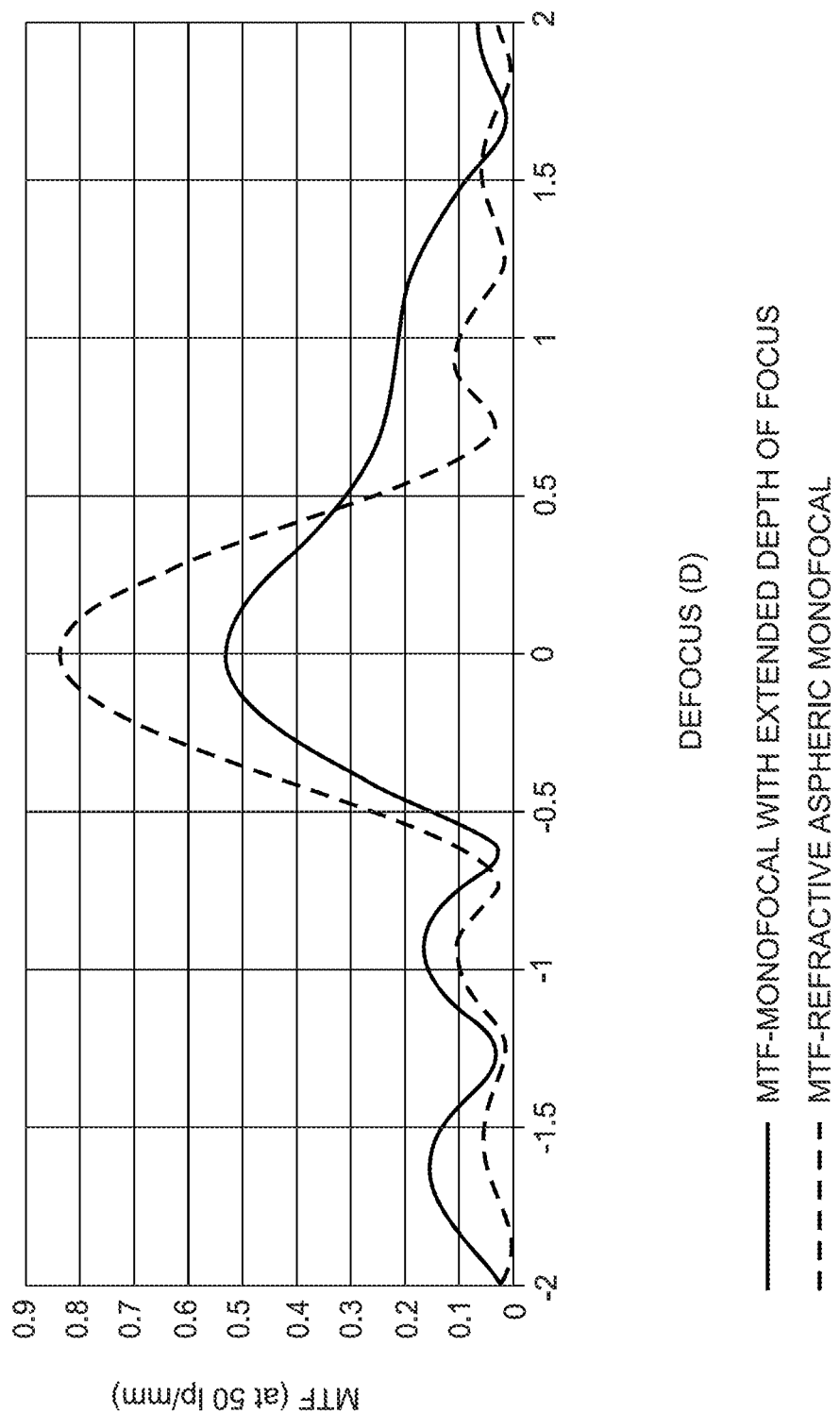
FIG. 4 illustrates through-focus MTF plots (for 50 lp/mm at the retina) for the IOL in FIG. 1 and a refractive monofocal IOL without the combined diffractive profile respectively, and illustrates the monofocal nature as well as extended energy spread of lenses according to aspects of the present invention.

FIG. 4 shows through-focus MTF plots of the EDOF IOL in FIG. 2 and a refractive monofocal IOL for comparison. The refractive monofocal used for comparison has the same prescription as the base refractive lens of the EDOF lens and excludes the combined diffractive profile (see the base refractive lens prescription above).

FIG. 4 illustrates the monofocal nature of lenses according to aspects of the present invention, as well as the spread of energy along the myopic side of optical axis caused by lenses according to aspects of the present invention. MTFs may be calculated in a straightforward numerical manner, either by a raytracing program such as Oslo® from Sinclair Optics of Pittsford N.Y. or Zemax from Zemax, LLC of Kirkland, Wash. or by another existing simulation tool, or by self-written code, all of which provide equivalent results using different calculation techniques.

FIG. 4 is a plot of the through-focus MTF at 50 line pairs per mm and using a 3 mm pupil aperture. The plot provides a measure of the spread of optical energy around the focal region on the optical axis. It is to be appreciated that to measure depth of focus, as illustrated in FIG. 4, requires the use of a model eye in which the intraocular lens is located either as a physical sample or as a computational model.

Figure 5:
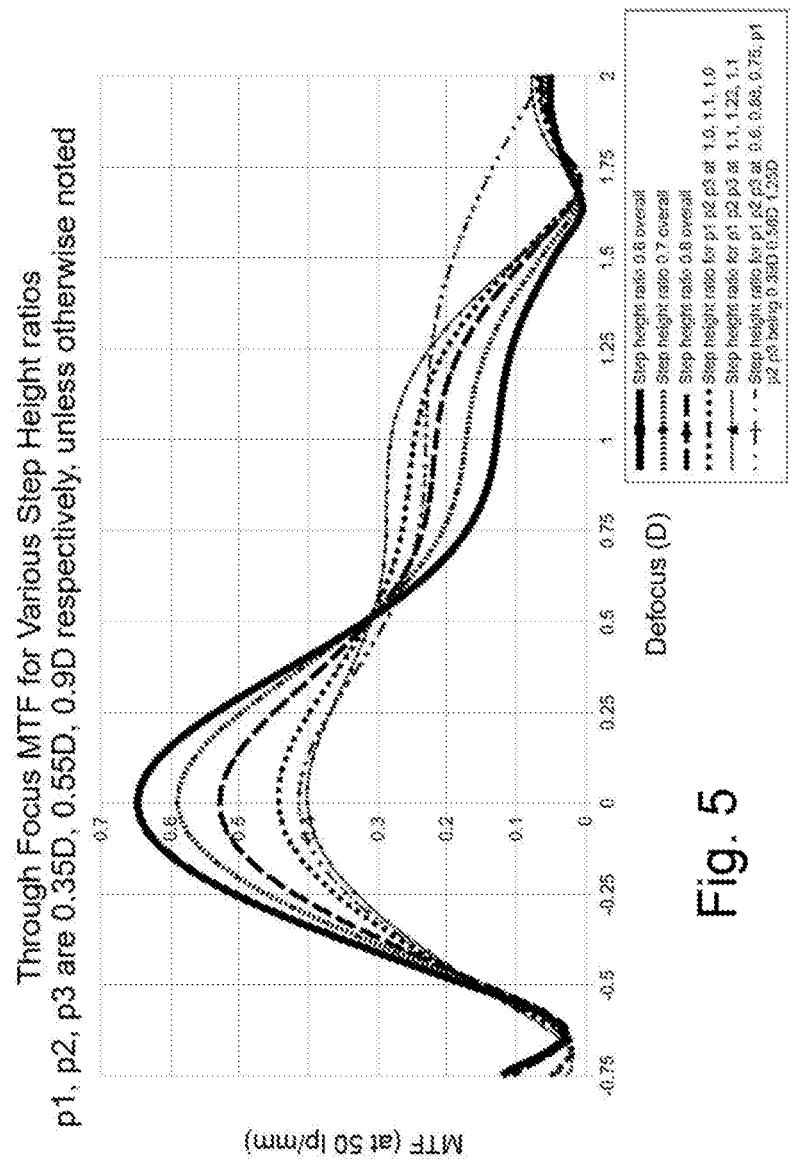
FIG. 5 illustrates through-focus MTF plots (for 50 lp/mm at the retina) of examples of lenses according to aspects of the present invention where each lens is selected to have a given phase delay η or multiple different phase delays, such as one for each constituent profile.

The through-focus MTF curves in FIG. 4 and FIG. 5 are generated using computational models of the intraocular lenses specified above, in a model eye defined as Model Eye 1 in the ISO 11979-2 2014 standard for intraocular lenses. Since lens and model eye aberrations can result in some extension in depth of focus, for the illustration purposes, the model and the base refractive lens are selected such that the extension in depth of focus provided by the invented diffractive profile in FIG. 2 is not obscured, for example by presence of spherical aberration. Accordingly, the ISO Model Eye 1 was used in the examples described herein because it provides a minimal amount of spherical aberration in the cornea present therein, and the base refractive lens was selected to have an amount of spherical aberration of an opposite sign to cancel what little spherical aberration is present in Model Eye 1. While the base refractive lens used for illustration above includes a low amount aberration selected to cancel the spherical aberration of Model 1, such a configuration was selected solely illustration purposes. Lenses according to aspects of the present invention may have any suitable amount of spherical aberration that doesn't frustrate other aspects of the lens. It will be appreciated that such spherical aberration can enhance a depth of focus in a conventional manner when used in combination with features according to aspects of the present invention. The choice of 3 mm for the aperture diameter, used in the model eye for the simulations for FIG. 4 and FIG. 5, represents a typical pupil size in the human eye under photopic conditions.

As seen in FIG. 4, the MTF of the extended depth of focus lens shows a depth of focus of 1.16 D from the MTF focal peak at zero defocus (i.e., an absolute maximum corresponding to best focus) using the 0.2 MTF units minimum level on the positive (i.e., myopic) defocus power side. For the MTF of the refractive aspheric monofocal without a diffractive EDOF structure in FIG. 4, the depth of focus at the 0.2 level on the myopic side is 0.53 D. Assuming that objects at infinite distance are at best focus (i.e., at the peak MTF), the depth of focus on the negative or hyperopic defocus power side is considered lost since it cannot be used in human vision.

Another feature of the MTF of the extended depth of focus monofocal in FIG. 4 is the absence of MTF dips below the 0.2 MTF level between the focal peak at zero defocus and 1.16D defocus thus supporting useful vision between the lens focus and its depth of focus limit. It is to be noted that the MTF of the EDOF lens in FIG. 4 has an absolute maximum peak at an MTF level of 0.53 MTF units which is below the absolute maximum peak of the MTF of the refractive aspheric monofocal without the combined diffractive profile; however, at the peak, the MTF of the EDOF lens has a great enough value to provide uncompromised vision to the wearer. The monofocal nature of the MTF extended depth of focus monofocal in FIG. 4 is illustrated through its single peak (i.e., the absolute maximum corresponding to best focus) before the first zero in the MTF and is expected to minimize visual disturbances and confusion experienced by users of multifocal intraocular lenses.

FIG. 5 illustrates through-focus MTF plots of examples of lenses according to aspects of the present invention where the constituent diffractive profiles of each lens are selected to have one or more corresponding phase delays $\eta$ (specified as a fraction of a 546 nm wavelength). In one embodiment, the phase delay $\eta=0.6$ for each of the profiles $p_1=0.35D$, $p_2=0.55D$ and $p_3=0.9D$. In another of the embodiments, the phase delay $\eta=0.7$ for each of the profiles $p_1=0.35D$, $p_2=0.55D$ and $p_3=0.9D$. In yet another embodiment, the phase delay $\eta=0.8$ for each of the profiles $p_1=0.35D$, $p_2=0.55D$ and, $p_3=0.9D$. In still another embodiment, the phase delay $\eta=1.0$ for the profile $p_1=0.35D$, the phase delay $\eta=1.1$ for the profile $p_2=0.55D$ and, the phase delay $\eta=1.0$ for the profile $p_3=0.9D$. In still another embodiment, the phase delay $\eta=1.1$ for the profile $p_1=0.35D$, the phase delay $\eta=1.22$ for the profile $p_2=0.55D$ and, the phase delay $\eta=1.1$ for the profile $p_3=0.9D$. In another embodiment, the profiles are constructed such that a profile $p_1=0.39D$ has a phase delay $\eta=0.6$, a profile $p_1=0.58D$ has a phase delay $\eta=0.88$ and, a profile $p_1=1.25D$ has a phase delay $\eta=0.75$ for 546 nm light.

It is to be appreciated from FIG. 5 that the shape of the through-focus MTF curve is sensitive to the value(s) $\eta$. It is also to be appreciated that, in the illustrated examples, there is shorter depth of focus for $\eta$ of 0.6 and broad MTF profile with an increased depth of focus as $\eta$ approaches a value of 1.2. However, each of the illustrated lens embodiments exhibits an extended depth of focus. Furthermore, three of the curves in FIG. 5 correspond to lenses where MTF curves demonstrate that constituent diffractive profiles of a given combined profile can have different values of $\eta$ than one another. In some embodiments, the depth of focus is greater than 0.85 diopters when in Model Eye 1. In other embodiments it is greater than 1.0 diopter. In still others it is greater than 1.25 diopters. The depth of focus may be achieved in a lens that is without spherical aberration or in a lens with spherical aberration.

FIG. 5 illustrates through-focus MTF plots of examples of lenses according to aspects of the present invention where the constituent diffractive profiles of each lens are selected to have one or more corresponding phase delays $\eta$ (specified as a fraction of a 546 nm wavelength). In one embodiment, the phase delay $\eta=0.6$ for each of the profiles $p_1=0.35D$, $p_2=0.55D$ and $p_3=0.9D$. In another of the embodiments, the phase delay $\eta=0.7$ for each of the profiles $p_1=0.35D$, $p_2 0.55D$ and $p_3 0.9D$. In yet another embodiment, the phase delay $\eta=0.8$ for each of the profiles $p_1=0.35D$, $p_2=0.55D$ and, $p_3=0.9D$. In still another embodiment, the phase delay $\eta=1.0$ for the profile $p_1=0.35D$, the phase delay $\eta=1.1$ for the profile $p_2=0.55D$ and, the phase delay $\eta=1.0$ for the profile $p_3=0.9D$. In still another embodiment, the phase delay $\eta=1.1$ for the profile $p_1=0.35D$, the phase delay $\eta=1.22$ for the profile $p_2=0.55D$ and, the phase delay $\eta=1.1$ for the profile $p_3=0.9D$. In another embodiment, the profiles are constructed such that a profile $p_1=0.39D$ has a phase delay $\eta=0.6$, a profile $p_2=0.58D$ has a phase delay $\eta=0.88$ and, a profile $p_3=1.25D$ has a phase delay $\eta=0.75$ for 546 nm light.

Figure 6:
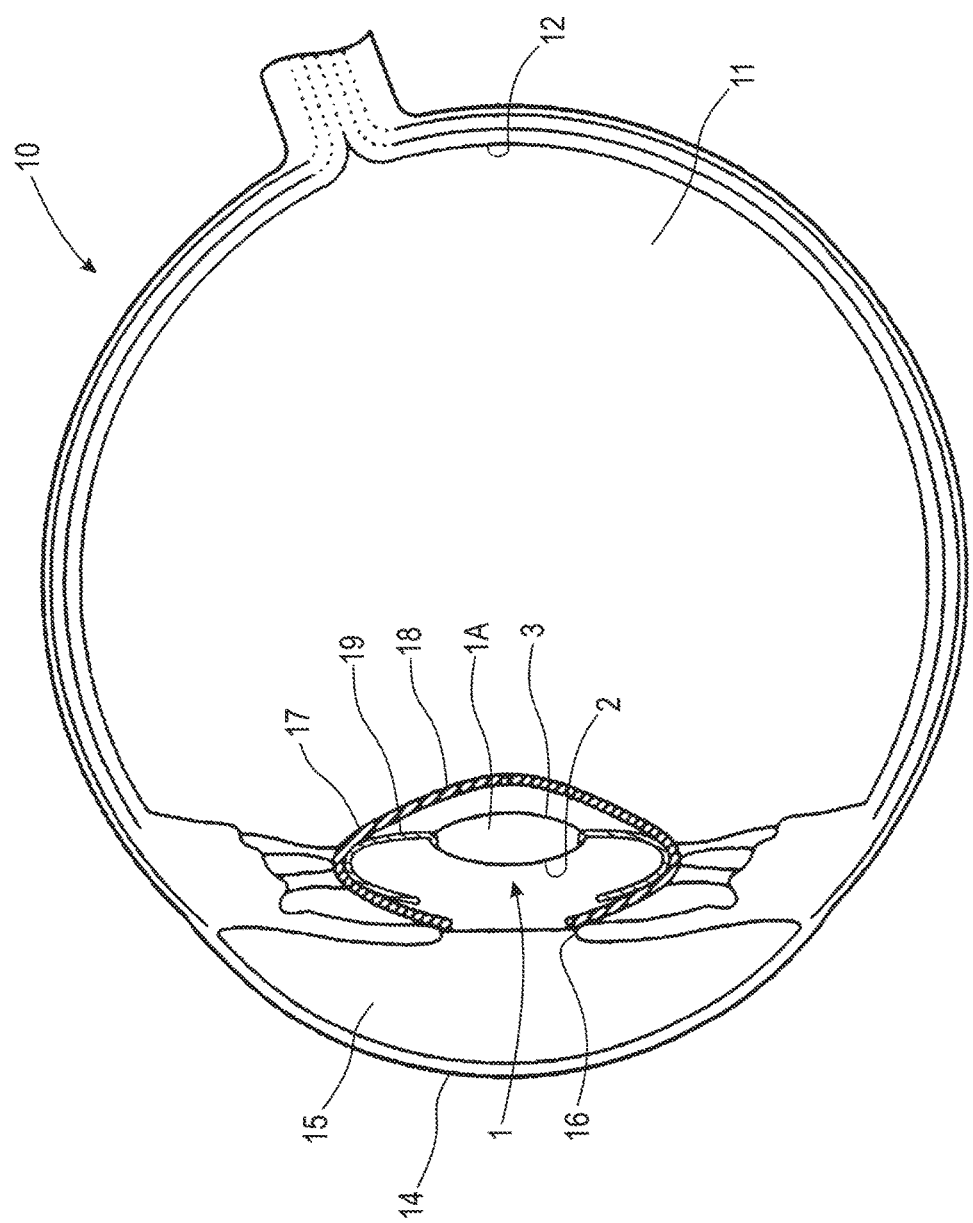
FIG. 6 is a schematic illustration of a human eye after a natural lens has been removed and an intraocular lens according to aspects of the present invention has been surgically implanted in the capsular bag of the eye.

FIG. 6 shows a human eye 10, after an intraocular lens 1 according to aspects of the present invention has been surgically implanted. Light enters from the left of FIG. 6, and passes through cornea 14, anterior chamber 15, iris 16, and enters capsular bag 17. Capsular bag 17 houses intraocular lens 1 in addition to aqueous fluid which occupies the remaining volume and equalizes the pressure in the eye 10. After passing through intraocular lens 1, light exits posterior wall 18 of the capsular bag 17, passes through posterior chamber 11, and strikes retina 12. The retina detects the light and converts it to a signal transmitted through optic nerve 8 to the brain.

Intraocular lens 1 has an optic 1a that has a refractive index greater than the aqueous fluid that surrounds it and, typically, the refractive power of an intraocular lens is in the range of about 5 Diopters to about 30 Diopters to compensate for the loss of natural lens which it typically replaces.

Optic 1a has an anterior surface 2 facing away from the retina 12 and a posterior surface 3 facing toward the retina 12. As illustrated, an optic 1a is held in place by one or more haptics 19, which couple optic 1a to the capsular bag 19. The one or more haptics may be of any known or yet to be developed configuration (e.g., plate, wire, C-loop, J-loop), and may be of an accommodating or non-accommodating type. In some embodiments, the IOL may have no haptics.

Optic 1a intraocular lens 1 may be disposed adjacent to, and even pressed against, the posterior wall 18, for example, to reduce cellular growth on optic 1a. Alternatively, optical 1a may be positioned within the capsular bag 17 in a position spaced away from the posterior wall 18, for example, to allow accommodative movement of optic 1a of the intraocular lens 1 along the optical axis (i.e., the lens is as an accommodative IOL); however, it will be appreciated that advantages of the extended depth of focus features of the lenses according to aspects of the present invention facilitate extended vision without complications that may result from accommodative movement.

A well-corrected eye forms an image of a distant object (i.e., an object at optical infinity) at retina 12. If the lens has too much or too little power, the image shifts axially along the optical axis away from retina 12 a corresponding distance toward or away from lens 1. Note, the power required to focus a close or near object onto the retina is greater than the power required to focus a distant or far object onto the retina.

In some instances lenses having diffractive profiles as set forth above are provided on each lens of an intraocular lens set. The lenses of the set have different base powers (i.e., refractive powers) than one another. A lens set has a range of dioptric powers of at least 10 diopters, and comprises at least three lenses. In some embodiments, the lenses of the lens set have a same combined diffractive profile on each lens (i.e., the lenses have different refractive power and the same combined diffractive profile disposed thereon to provide an enhanced depth of field). For example, the refractive powers of the lens set may range from 10D to 30D, the lenses having increments of 0.5D (i.e., 41 lenses).

It will be appreciated that several of the above-disclosed features and functions, or alternatives thereof, may be desirably combined into many other different systems or applications. Also that various presently unforeseen or unanticipated alternatives, modifications, variations, or improvements therein may be subsequently made by those skilled in the art which are also intended to be encompassed by the following claims.

What is claimed is:

1. A monofocal intraocular lens, comprising:
an optic having an anterior surface and a posterior surface, providing a refractive base power, at least one of the anterior surface and the posterior surface having disposed thereon a combined profile comprising steps having heights determined by combining three constituent diffractive profiles, the diffractive profiles corresponding to powers p1, p2 and p3, the powers being different than one another and each power being a positive power less than about 1D, and each of the diffractive profiles having step heights causing a phase delay, relative to aqueous fluid, of 0.6 to 1.2 times $2\pi$ for 546 nm light, the combined profile defined by the function:

$$z=\max(\text{diffractive profile}(p1), \text{diffractive profile}(p2), \text{diffractive profile}(p3)),$$

where p3>p2>p1.

2. The lens of claim 1, wherein the combined profile is disposed completely on the anterior surface of the lens.

3. The lens of claim 1, wherein the combined profile is disposed piecewise on both the anterior surface and posterior surface of the lens.

4. The lens of claim 1, wherein the combined profile is rotationally symmetric.

5. The lens of claim 1, wherein zones of the lens formed by the three constituent profiles are kinoform in shape.

6. The lens of claim 1, wherein each of the diffractive profiles has step heights causing a phase delay, relative to aqueous fluid, of 0.8 to 1.0 times $2\pi$ for 546 nm light.

7. The lens of claim 1, wherein the central zone has a refractive surface having a shape independent of the constituent diffractive profiles.

8. The lens of claim 1, wherein the ratio of $p_1$ to $p_2$ is about 0.6, and the ratio $p_1$ to $p_3$ is about 0.4.

9. The lens of claim 1, wherein the ratio of $p_1$ to $p_2$ is about 0.67, and the ratio $p_1$ to $p_3$ is about 0.31.

10. The lens of claim 1, wherein the depth of focus is greater than 0.85 diopters.

11. The lens of claim 8, wherein the depth of focus is greater than 0.85 diopters.

12. A monofocal intraocular lens, comprising:
an optic having an anterior surface and a posterior surface, providing a refractive base power, at least one of the anterior surface and the posterior surface having disposed thereon a combined profile comprising steps having heights determined by combining three constituent diffractive profiles, the diffractive profiles corresponding to powers p1, p2 and p3, the powers being different than one another and each power being a positive power less than about 1.25D, and each of the diffractive profiles having step heights causing a phase delay, relative to aqueous fluid, of 0.6 to 1.2 times $2\pi$ for 546 nm light, the combined profile defined by the function:

$$z=\max(\text{diffractive profile}(p1), \text{diffractive profile}(p2), \text{diffractive profile}(p3)),$$

where p3>p2>p1.

13. The lens of claim 12, wherein the combined profile is disposed completely on the anterior surface of the lens.

14. The lens of claim 12, wherein the combined profile is disposed piecewise on both the anterior surface and posterior surface of the lens.

15. The lens of claim 12, wherein the combined profile is rotationally symmetric.

16. The lens of claim 12, wherein zones of the lens formed by the three constituent profiles are kinoform in shape.

17. The lens of claim 12, wherein each of the diffractive profiles has step heights causing a phase delay, relative to aqueous fluid, of 0.8 to 1.0 times $2\pi$ for 546 nm light.

18. The lens of claim 12, wherein the central zone has a refractive surface having a shape independent of the constituent diffractive profiles.

19. The lens of claim 12, wherein the ratio of $p_1$ to $p_2$ is about 0.6, and the ratio $p_1$ to $p_3$ is about 0.4.

20. The lens of claim 12, wherein the ratio of $p_1$ to $p_2$ is about 0.67, and the ratio $p_1$ to $p_3$ is about 0.31.

21. The lens of claim 12, wherein the depth of focus is greater than 0.85 diopters.

22. The lens of claim 19, wherein the depth of focus is greater than 0.85 diopters.

23. A set of monofocal intraocular lenses, comprising at least three lens, each of the lenses comprising an optic having an anterior surface and a posterior surface, providing a refractive base power, at least one of the anterior surface and the posterior surface having disposed thereon a combined profile comprising steps having heights determined by combining three constituent diffractive profiles, the diffractive profiles corresponding to powers p1, p2 and p3, the powers being different than one another and each power being a positive power less than about 1.25D, and each of the diffractive profiles having step heights causing a phase delay, relative to aqueous fluid, of 0.6 to 1.2 times $2\pi$ for 546 nm light, the combined profile defined by the function:

$z=\max(\text{diffractive profile}(p1),\text{diffractive profile}(p2),\text{diffractive profile}(p3))$, where p3>p2>p1, each of the lenses of the set having a different refractive, base dioptric power than one another, the range of the refractive base powers being at least 10 diopters, and the combined profile of each of the at least three lenses being same as one another.

24. The set of intraocular lenses of claim 23, wherein the combined profile on each of the at least three lenses is the same as the combined profile of each of the other of the at least three lenses.

25. A monofocal intraocular lens, comprising:

an optic having an anterior surface and a posterior surface to provide a refractive base power, at least one of the anterior surface and the posterior surface having disposed thereon a profile comprising diffractive steps, wherein, when the lens is placed in a physical model eye, a through-focus modulation transfer function (MTF) of the eye model, for a spatial frequency of 50 lp/mm, has a peak characterized by a slope of zero, and the MTF has a range extending in a myopic direction from the peak over which the MTF has a value greater than 0.2 MTF unit, the range being greater than 1.25D, the peak being the only peak in the MTF before a first zero in the MTF.

\* \* \* \* \*